(12) United States Patent
Grant et al.

(10) Patent No.: US 10,159,454 B2
(45) Date of Patent: Dec. 25, 2018

(54) CONTRAST AGENT PERFUSION ADAPTIVE IMAGING SYSTEM

(75) Inventors: Katharine Lynn Rowley Grant, Rochester, MN (US); Bernhard Schmidt, Fürth (DE)

(73) Assignee: Siemens Healthcare GmbH, Erlangen (DE)

( * ) Notice: Subject to any disclaimer, the term of this patent is extended or adjusted under 35 U.S.C. 154(b) by 377 days.

(21) Appl. No.: 13/594,943

(22) Filed: Aug. 27, 2012

(65) Prior Publication Data

US 2013/0066198 A1 Mar. 14, 2013

Related U.S. Application Data

(60) Provisional application No. 61/532,587, filed on Sep. 9, 2011.

(51) Int. Cl.
*A61B 6/00* (2006.01)
*A61B 6/03* (2006.01)

(52) U.S. Cl.
CPC .............. *A61B 6/481* (2013.01); *A61B 6/032* (2013.01); *A61B 6/486* (2013.01); *A61B 6/507* (2013.01); *A61B 6/5217* (2013.01)

(58) Field of Classification Search
CPC .. A61B 6/03; A61B 6/032; A61B 6/48; A61B 6/481; A61B 6/486
USPC ................... 424/9.3; 600/407, 410, 425, 427
See application file for complete search history.

(56) References Cited

U.S. PATENT DOCUMENTS

| 5,590,654 A | 1/1997 | Prince | |
|---|---|---|---|
| 5,749,259 A | 5/1998 | Hamouda et al. | |
| 7,467,006 B2 * | 12/2008 | Abe et al. | 600/420 |
| 7,534,210 B2 | 5/2009 | Chomas et al. | |
| 7,606,614 B2 | 10/2009 | Licato et al. | |
| 2003/0036694 A1 * | 2/2003 | Liu | 600/413 |
| 2005/0187476 A1 * | 8/2005 | Chomas et al. | 600/458 |
| 2007/0078333 A1 | 4/2007 | Takayuki et al. | |

FOREIGN PATENT DOCUMENTS

| CN | 101185591 A | 5/2008 |
|---|---|---|
| CN | 101889872 A | 11/2010 |
| WO | 2010058014 A1 | 5/2010 |

OTHER PUBLICATIONS

Office Action dated Mar. 19, 2015 in CN Application No. 201210331685.9 (English translation included).

* cited by examiner

*Primary Examiner* — Tse Chen
*Assistant Examiner* — Jason Ip (57) ABSTRACT

An imaging system selects a medical imaging protocol using a repository of information associating multiple ranges of contrast agent peak time with corresponding different imaging protocols. An imaging protocol comprises a method for acquiring images using an imaging system and using data identifying at least one of (a) an imaging rate within an imaging scan cycle and (b) an interval between imaging scans. A contrast agent peak time comprises a time a contrast agent concentration substantially reaches a peak value in an anatomical region of interest of a patient relative to a time of start of contrast agent injection. A contrast agent peak time detector detects a contrast agent peak time. An imaging processor adaptively selects an imaging protocol from the imaging protocols in response to a comparison of a detected contrast agent peak time with at least one of the plurality of ranges.

20 Claims, 5 Drawing Sheets

CONTRAST AGENT PERFUSION ADAPTIVE IMAGING SYSTEM

This is a non-provisional application of provisional application Ser. No. 61/532,587 filed Sep. 9, 2011, by K. L. R. Grant et al.

FIELD OF THE INVENTION

This invention concerns a system for automatically adaptively selecting a medical image acquisition protocol usable by a Computed Tomography (CT), X-ray or other imaging system based on time duration it takes injected contrast agent to reach a peak concentration.

BACKGROUND OF THE INVENTION

The acquisition of images in the presence of contrast agent in known imaging systems (e.g. a CT (computed tomography) system) is limited by either acquisition time or number of image acquisition cycles. A common reoccurring issue is that the time to peak or enhancement of contrast agent is different for each patient and, scanning acquisitions need to begin before contrast agent is present in an image. In a majority of patients, a single, stable scan protocol is sufficient to properly gather necessary image data. In some patients, where their contrast agent "peaks" earlier than average, patients may be over-radiated due to acquisition of data beyond a necessary time point. In other patients, especially patients with poor/low cardiac output, their contrast agent peaks substantially later, resulting in a longer contrast agent "fall off" period, that gets "cut off"—not imaged. When the "tail" or fall off is not imaged, the calculated estimate for Cerebral Blood Volume (CBV) may be inaccurate, for example, causing problems or inaccuracies with diagnosis, and perhaps treatment. Further, the cases where this CBV inaccuracy occurs tend to be some of the most sensitive cases where an accurate CBV is most desirable.

Physicians address the contrast agent variation problem by imaging at longer time intervals (i.e., 5 sec instead of 3 sec), for example, allowing them to image for a longer duration up to 70 sec (instead of 40 or 45 sec). This interval allows collection of enough time points for these patients with later peaks, but results in over-radiation for some patients and reduced temporal resolution for other patients. Alternatively, for another subset of patients, a physician may start imaging earlier to catch a faster moving contrast bolus. Additionally, a physician in known systems needs to choose a post-processing method prior to scanning, as post-processing requires different amounts of data (in terms of frequency of collection and length of collection). Physicians do not typically have guidance as to how patient image data is to be post-processed. A system according to invention principles addresses these deficiencies and related problems.

SUMMARY OF THE INVENTION

A system monitors a contrast bolus, and detects a contrast agent peak in the parenchyma by determining the enhancement peak or shape in real-time (time-to-peak or slope) and adaptively adjusts an image acquisition rate and period in response to patient specific contrast agent timing (time-to-peak). Further, the inventors have advantageously recognized that in addition to physiological patient parameters, data identifying a type of post processing method may be used as either an additional input parameter to a patient scan protocol, or be determined automatically by a manner of acquisition. A computer implemented system automatically adaptively selects a medical image acquisition protocol usable by a Computed Tomography (CT), X-ray or other imaging system. A repository of predetermined information associates multiple ranges of contrast agent peak time with corresponding different image acquisition protocols. An image acquisition protocol comprises a method for acquiring images using an imaging system and using data identifying at least one of (a) an image acquisition rate within an imaging scan cycle and (b) an interval between imaging scans. A contrast agent peak time comprises a time a contrast agent concentration substantially reaches a peak value in an anatomical region of interest of a patient relative to a time of start of contrast agent injection. A contrast agent peak time detector detects a contrast agent peak time. An imaging processor adaptively selects an image acquisition protocol from the image acquisition protocols in response to a comparison of a detected contrast agent peak time with at least one of the plurality of ranges. An imaging processor adaptively selects a post-processing method from different post-processing methods in response to an image acquisition protocol applied and patient medical condition and patient parameters.

DETAILED DESCRIPTION OF THE INVENTION

Definition

Hounsfield unit (HU)—indicates X-ray radiation absorption and attenuation of CT scanner radiation on a scale comprising a linear transformation of an original linear attenuation coefficient measurement into one in which the radiodensity of distilled water at standard pressure and temperature (STP) is defined as zero Hounsfield units (HU), while the radiodensity of air at STP is defined as −1000 HU. In a voxel with average linear attenuation coefficient, the corresponding HU value is therefore given by:

$$HU = 1000 \times \frac{\mu_X - \mu_{water}}{\mu_{water}}$$

Where $\mu_{water}$ is the linear attenuation coefficient of water.

A system according to invention principles monitors a contrast bolus, and detects a contrast agent peak in the parenchyma by determining the peak in real-time (time-to-peak). The system adaptively adjusts an image acquisition rate and period in response to patient specific contrast agent timing (time-to-peak). The acquisition rate in one embodiment is selected by a user if there is a priori information on a patient condition.

Figure 1:
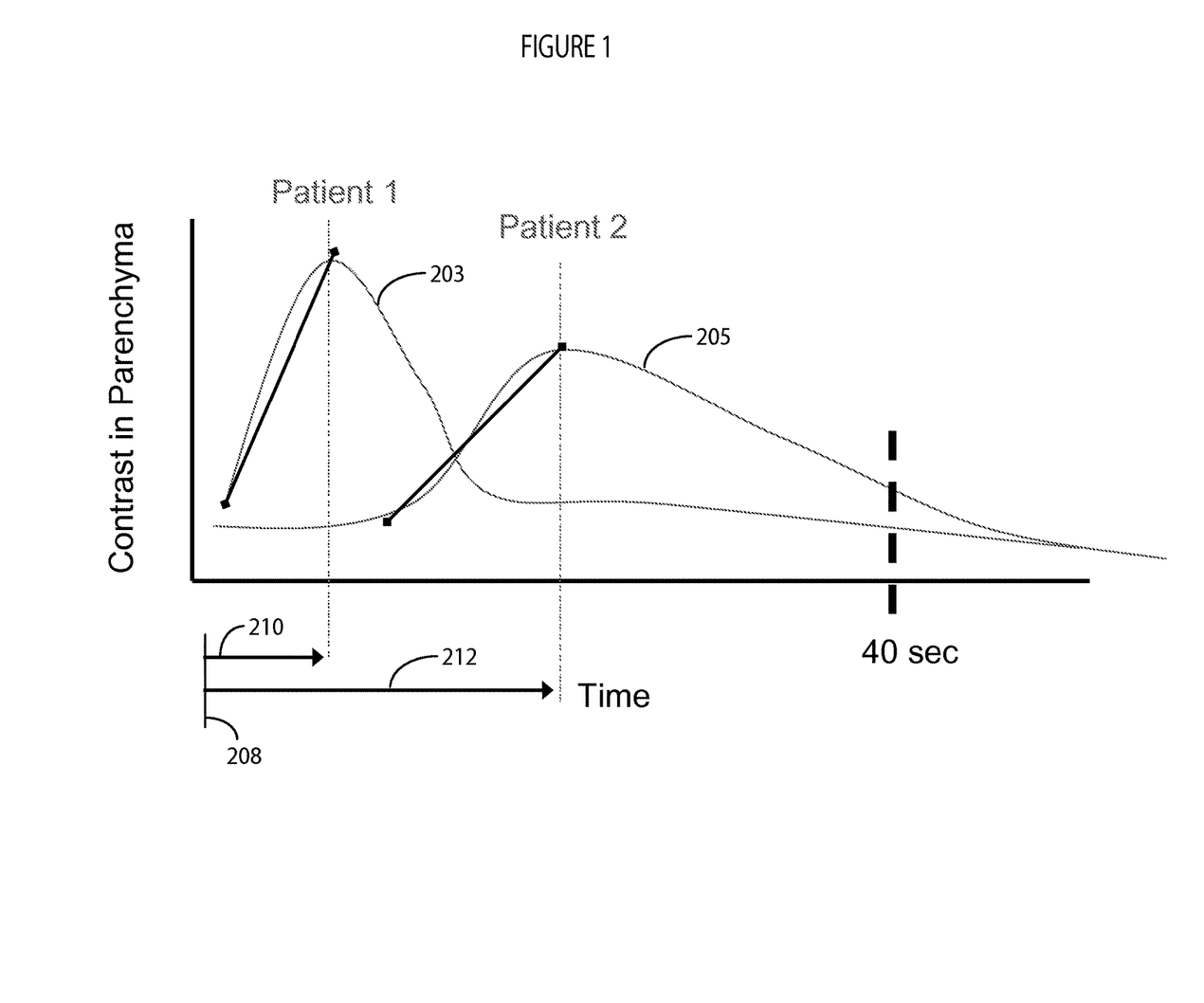
FIG. 1 shows graphs of luminance contrast of a parenchyma of two different patients over time following contrast agent introduction to a patient vessel and indicating different time-to-peak contrast for the two patients.
Figure 2:
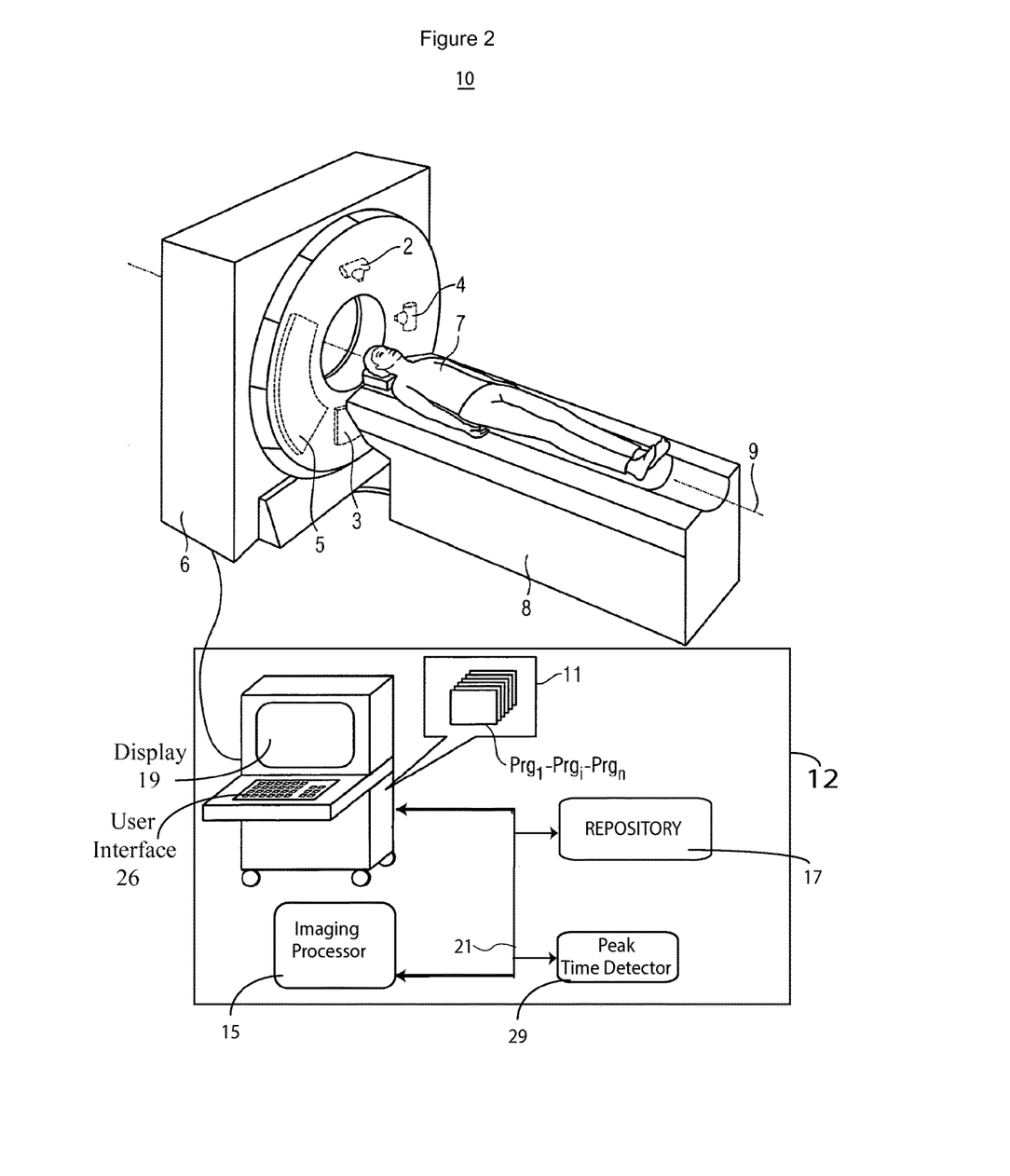
FIG. 2 shows a computer implemented system for automatically adaptively selecting a medical image acquisition protocol usable by a Computed Tomography (CT), X-ray or other imaging system, according to invention principles.

FIG. 1 shows graphs 203, 205 of luminance contrast of a parenchyma of two different patients over time following contrast agent introduction to a patient vessel and indicating different time-to-peak contrast for the two patients. The time-to-peak 210, 212 from time of introduction 208 of contrast agent for contrast in the parenchyma is much longer for patient 2 (curve 205) than patient 1 (curve 203). If image acquisition ended at 40 seconds as it would for an average patient (patient 1), a significant amount of perfusion information is lost (area under curve 205 to the right of the 40 second cut off). Slope of curve 205 of patient 2 is lower than slope for curve 203 in patient 1, indicating that images need to be collected for a longer period of time than a "normal" scan in order to obtain necessary information FIG. 2 shows computer implemented system 10 for automatically adaptively selecting a medical image acquisition protocol usable by a Computed Tomography (CT), X-ray or other imaging system. In one embodiment for example, from start of image acquisition of a region of anatomy to peak of a contrast agent in the region of anatomy, images are acquired at 5 second intervals. In response to detection of a contrast agent peak, the system automatically acquires images at an 8 second interval (or at a 5 second interval if a peak occurs at a "normal" time-to-peak). In another embodiment, system 10 continues image acquisition at the same 5 second interval rate, but images are acquired for a longer time duration during this interval. System 10 also monitors contrast agent luminance dropping below a predetermined threshold level and ends an imaging scan earlier than a preset time, or extends image acquisition beyond a preset time to minimize radiation dose and maximize image data collection of necessary and useful information. In another embodiment, the system calculates the slope (gradient) of a contrast agent bolus concentration curve at different points in time and compares the slope to an average or expected slope at the different time points. A higher than average slope represents a faster "time-to-peak", whereas a lower than average slope indicates a slower "time-to-peak" requiring a longer image acquisition period.

CT system 10 has a gantry housing 6 and a displaceable patient support table 8 and includes processing unit 12 (e.g., a workstation or portable device such as a notebook, Personal Digital Assistant, phone) for operating the CT system and performing image data processing. Processing unit 12 includes at least one repository 17, imaging processor 15 and peak time detector 29. A patient 7 is located on displaceable patient support table 8 that is movable during a scan along system axis 9 through a measuring field between X-ray tube 2 and X-ray radiation detector 3 opposite the tube across the CT imaging unit bore, while the X-ray tube 2 and the detector 3 move in a fashion rotating about the patient 7. CT system 10 supports spiral, axial and other scanning modes for imaging patient 7. Multiple X-ray tubes exemplified by second X-ray tube 4 and the detector 5 lying opposite may be used for scanning.

In order to control the CT system 10 and to evaluate the detector data received, computer programs (machine readable instructions) Prg1 to Prgn are executed by processing unit 12 to perform methods supporting operation of system 10. Prg1 to Prgn are stored in memory 11 in processing unit 12. Processing unit 12 includes display 19 for presenting output data provided by the system. Unit 12, or one or more other units of system 10 inter-communicating via network 21, store predetermined information in at least one repository 17. Specifically, repository 17 stores predetermined information associating multiple ranges of contrast agent peak time with corresponding different image acquisition protocols. An image acquisition protocol comprises a method for acquiring images uses an imaging system and using data identifying at least one of (a) an image acquisition rate within an imaging scan cycle and (b) an interval between imaging scans. A contrast agent peak time comprises a time a contrast agent concentration substantially reaches a peak value in an anatomical region of interest of a patient relative to a time of start of contrast agent injection. Peak time detector 29 detects a contrast agent peak time. Imaging processor 15 adaptively selects an image acquisition protocol from the image acquisition protocols in response to a comparison of a detected contrast agent peak time with at least one of the multiple ranges.

Processor 15 receives data identifying a type of imaging procedure or an anatomical region to be imaged and further uses the information in automatically detecting contrast agent peak time and substantially immediately in real time selecting between imaging protocols e.g. first and second protocols in response to detected peak time. Processor 15 provides output data to a destination device indicating contrast agent parameters for use in administering contrast agent to a patient. Processing unit 12 includes a user interface control device 26 such as a keyboard, mouse, touchscreen and voice data entry and interpretation device. System 10 comprises a CT scan (or in another embodiment an X-ray) modality imaging system and provides patient medical images. The medical images are generated in response to predetermined user (e.g., physician) specific preferences. At least one repository 17 stores medical image studies for multiple patients in DICOM compatible (or other) data format. A medical image study individually includes multiple image series of a patient anatomical portion which in turn individually include multiple images. In alternative arrangements, one or more of the units in unit 12 may be located on another device connected to network 21.

In operation, imaging processor 15 automatically adaptively selects a first medical image acquisition protocol for Topogram (scout) imaging. System 10 initiates a dynamic scan (CT or otherwise) may be synchronized with start of injection of contrast agent into tissue or a vessel of a region of interest (ROI) of a patient. System 10 detects a contrast agent peak or shape or slope during the scan by detecting a zero gradient point in contrast agent concentration in the ROI from a change in slope from increasing luminance contrast (increasing darkness of pixel luminance intensity) to decreasing luminance contrast (decreasing darkness of pixel luminance intensity). System 10 monitors an area within the ROI, looking for a pre-determined level of contrast agent to be present within the ROI. Imaging processor 15 advantageously records and monitors the Hounsfield unit (HU) values associated with radiation attenuation and presence of contrast agent within the ROI.

In response to detection of a time of contrast agent concentration peak (or once the average Hounsfield unit (HU) value of the ROI declines), processor 15 records this time relative to time of start of contrast agent injection. The peak time (time from contrast agent injection to time of peak detection) is compared in real time (i.e. substantially immediately) to an average expected time to peak for a normal patient population. Alternatively, if the HU values are being recorded, the system determines the slope of change of these HU values over time and compares this slope to an "average" slope (for an average patient population or a population having similar demographic characteristics (age, weight, height, gender) to the patient). The imaging protocol may be adapted to take into account a user selected post processing method (such as deconvolution or other method).

If the measured peak time is greater than average (greater than 3 seconds difference, for example), (or the slope is less than average), the system initiates imaging a first imaging protocol involving change in duration of scan acquisition and sampling rate.

The first imaging protocol substantially immediately extends maximum allowable scan time (to 70 seconds, for example) and/or substantially immediately extends the number of allowable scan cycles (from 26 to 46 for example). The extensions allow for one of two or more changes to the protocol. One change comprises continuing to scan at the same image acquisition rate, continuously for a longer duration (increasing radiation exposure), and in another embodiment comprises use of a lower current setting of the radiation tube voltage during the time extension following peak detection. Another change comprises using a different, lower sampling rate (cycle time), i.e., cycle time of approximately 3 seconds, or a multiple of an original cycle time.

If the measured peak time is less than average (having greater than 5 seconds difference, for example), (or the slope is greater than average), imaging processor 15 initiates a second different imaging protocol involving change in duration of scan acquisition. The second imaging protocol substantially immediately changes the duration of the scan (by reducing number of scan cycles), i.e., shortens scan time by 6 seconds. If the measured peak time or slope is within a certain range of the average, imaging processor 15 continues with the original (e.g. default) imaging protocol involving continuously scanning up to 40 seconds, at a preset sampling rate (cycle time of approximately 1.5 seconds) for the patient having particular demographic characteristics and medical conditions.

The default imaging protocol is likely to be more frequently used than the two alternative imaging protocols since the default protocol is optimized to an average patient population, and the majority of the patients fall within the original protocol candidate pool. The majority of the remainder of a patient population fall into a candidate pool for the first or second modified imaging protocols. The number of patients that qualify for the modification comprising the first and second imaging protocols is relatively small. Patients with low or poor cardiac output or known heart disease are automatically assigned the first imaging protocol, e.g. in response to user selection of a displayed check box item by a user. For example, a user selects a box associated with, heart disease present? (yes or no) or poor cardiac function? (yes or no), or integrates an ECG signal at the beginning of the protocol, the system in one embodiment automatically employs the first imaging protocol, without use of contrast agent peak detection. In another embodiment, under circumstances where a specific post processing method is to be utilized, a user selects a box prior to scanning to indicate a post-processing method. For example, a Patlak model (yes or no) or deconvolution method? (yes or no) is selected prior to the scan, where the system in one embodiment automatically employs a first imaging protocol, without the use of contrast detection, or in another embodiment employs use of contrast agent peak or slope detection, but alters the scan duration or image acquisition frequency as required, specific to the post processing method. A Patlak model is an image processing model known to those of ordinary skill in the art.

Figure 4:
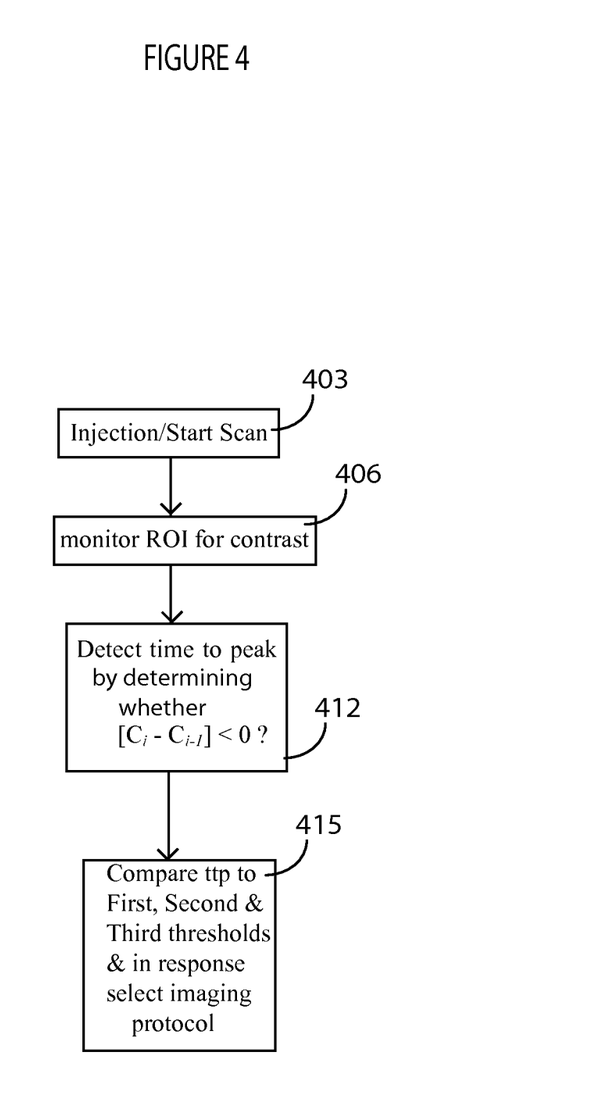
FIG. 4 shows a flowchart of a process used by a system for automatically determining a contrast agent peak concentration and adaptively selecting a medical image acquisition protocol, according to invention principles.

FIG. 4 shows a flowchart of a process used by a system for automatically determining a contrast agent peak concentration and adaptively selecting a medical image acquisition protocol. In step 403, contrast agent injection is initiated at the beginning of an imaging scan. Imaging processor 15 monitors luminance intensity of vessels in a ROI of acquired image data to determine contrast agent concentration in step 406. Processor 15 in step 412 detects time for the contrast agent to reach peak concentration from start of injection in step 403. Processor 15 determines an image and time for contrast agent to reach peak concentration based on direct comparison of the average HU of the ROI of an image acquired at a first acquisition time with the average HU of the ROI of a successively acquired image acquired at a second subsequent acquisition time.

Figure 3:
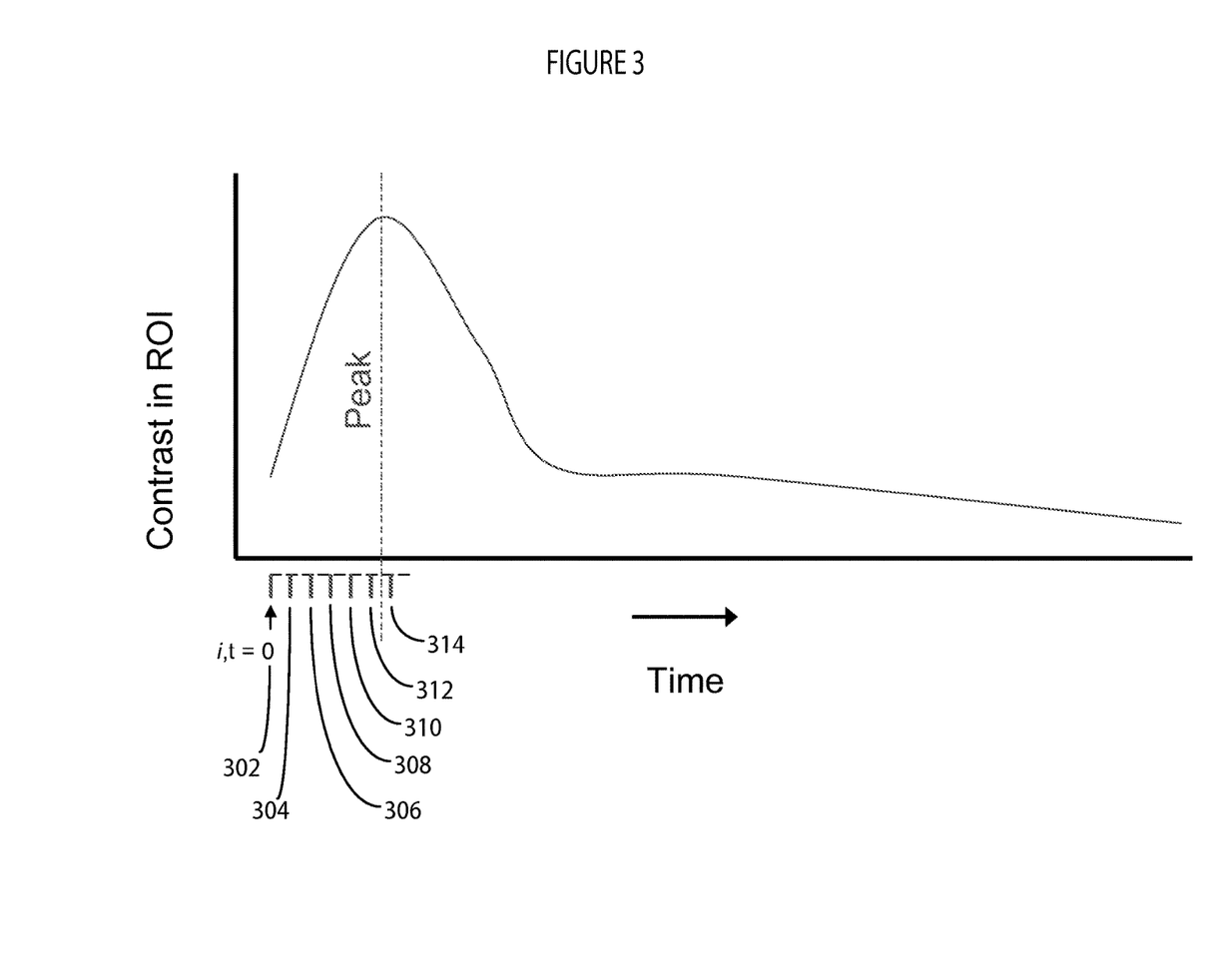
FIG. 3 illustrates determination of time to peak of contrast or determination of slope from start of an injection, according to invention principles.

FIG. 3 illustrates determination of time to peak contrast agent concentration from start of an injection at t=0 302 using images acquired at times t for i, 302, 304, 306, 308, 310, 312, 314 that are recorded by processor 15. The average HU of the ROI is getting larger if, $$[C_i - C_{i-1}] \geq 0,$$

where C is the luminance intensity or average HU for the pixels in the ROI, and i is the number of scan acquisitions, and t is the time of each scan acquisition, with t=0 seconds at injection initiation. The peak of contrast agent concentration is determined from when the average HU of the ROI stops getting larger as indicated by, $$[C_i - C_{i-1}] < 0.$$

Time-to-peak (ttp) contrast agent concentration in the ROI is, $$ttp = t_i = [C_i - C_{i-1}] < 0 = t6 = [C6 - C5] < 0$$

in the example of FIG. 3. In step 415 (FIG. 4), processor 15 compares the determined ttp to three different thresholds, for example, derived using an average time-to-peak contrast agent concentration tavg for a population of patients having similar demographic characteristics (age, weight, height, gender, pregnancy status) to select an imaging protocol for use in a patient examination. Specifically, if processor 15 determines $ttp \geq t_{avg} + 3$ seconds (approximately 2 heart cycles), processor 15 adaptively selects and initiates performance of the previously described first imaging protocol from multiple image acquisition protocols. If processor 15 determines $ttp < t_{avg} + 3$ seconds, and if $ttp \geq t_{avg} - 3$ seconds, processor 15 continues with the previously described original (e.g. default) imaging protocol. If $ttp \leq t_{avg} - 3$ seconds, processor 15 continues with the previously described original (e.g. default) imaging protocol but automatically ends the scan at t=35 seconds (instead of 40 seconds for example).

System 10 adaptively varies imaging protocol (e.g. sampling rate and interval) in response to measured or predicted time interval of peak contrast agent occurrence following start of contrast agent injection as well as in response to patient demographics including, age, weight gender, also patient known medical conditions. The system in one embodiment, predicts contrast agent peak and total perfusion time and adaptively varies imaging protocol e.g. using a 5 second interval between image acquisition before contrast agent peak and an 8 second interval between image acquisition after it. Imaging processor 15 also selects termination time and start time and duration of imaging to avoid overexposure and to ensure images are acquired of the contrast agent tail. Processor 15 selects an imaging protocol using a lookup table associating different protocols (different image acquisition intervals and rate) with different patient contrast agent peak times (measured and predicted based on contrast agent concentration gradient at particular times from start of injection), patient demographic characteristics and medical conditions.

Figure 5:
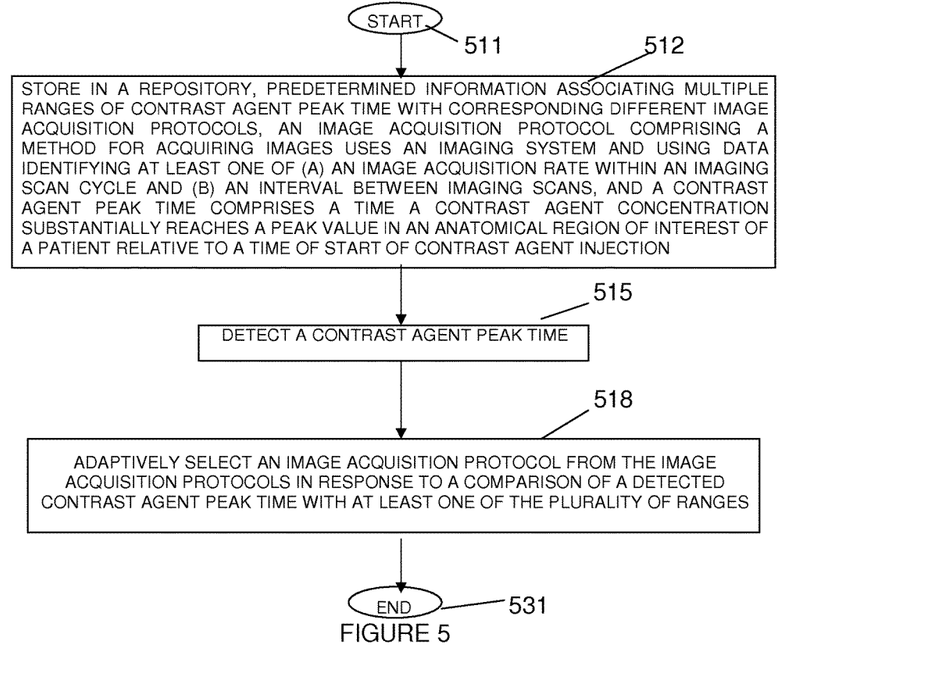
FIG. 5 shows a flowchart of a process used by a system for automatically adaptively selecting a medical image acquisition protocol usable by a Computed Tomography (CT), X-ray or other imaging system, according to invention principles.

FIG. 5 shows a flowchart of a process used by system 10 (FIG. 2) for automatically adaptively selecting a medical image acquisition protocol usable by a Computed Tomography (CT), X-ray or other imaging system. In step 512 following the start at step 511, processor 15 stores in repository 17 predetermined information associating multiple ranges of contrast agent peak time with corresponding different image acquisition protocols. An image acquisition protocol comprises a method for acquiring images using imaging system 10 and using data identifying at least one of (a) an image acquisition rate within an imaging scan cycle and (b) an interval between imaging scans. A contrast agent peak time comprises a time a contrast agent concentration substantially reaches a peak value in an anatomical region of interest of a patient relative to a time of start of contrast agent injection.

In step 515, contrast agent peak time detector 29 detects a contrast agent peak time. Imaging processor 15 in step 518 adaptively selects an image acquisition protocol from the image acquisition protocols in response to a comparison of a detected contrast agent peak time with at least one of the multiple ranges. Imaging processor 15 adaptively selects an image acquisition protocol increasing total imaging scanning time period of the anatomical region of interest, an increased time interval between scanning cycles and a reduced X-ray radiation tube voltage, in response to determining the detected contrast agent peak time exceeds a range associated with a normal patient. Imaging processor 15 adaptively selects an image acquisition protocol decreasing total imaging scanning time period of the anatomical region of interest, in response to determining the detected contrast agent peak time is lower than a range associated with a normal patient.

Processor 15 also adaptively selects an image acquisition protocol increasing total imaging scanning time of the region of interest, in response to predetermined information indicating the patient has a heart function impairment related condition. Further, processor 15 continues use of the existing image acquisition protocol without change, in response to determining the detected contrast agent peak time lies within a range associated with a normal patient. The range associated with the normal patient is a range associated with a normal patient having the demographic characteristics and medical conditions of the patient concerned for a prescribed imaging examination. The demographic characteristics include at least one of, age, weight, gender and pregnancy status. The medical conditions include at least one of, heart disease and impaired cardiac function. The process of FIG. 5 terminates at step 531.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication there-between. Computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s). A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of the FIGS. 2-5 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A system detects a contrast agent peak in vessels by determining the peak in real-time (time-to-peak) and adaptively varies imaging protocols including image acquisition rate and period before and after the peak and also predicts time-to-peak for a patient based on patient demographic characteristics and medical conditions. Further, the processes and applications may, in alternative embodiments, be located on one or more (e.g., distributed) processing devices on a network linking the units of FIG. 2. Any of the functions and steps provided in FIGS. 2-5 may be implemented in hardware, software or a combination of both. No claim element herein is to be construed under the provisions of 35 U.S.C. 112, sixth paragraph, unless the element is expressly recited using the phrase "means for."

What is claimed is:

1. A computer implemented system for automatically adaptively selecting a medical image acquisition protocol usable by a Computed Tomography (CT) or X-ray imaging system, comprising:
   an imaging system of a Computed Tomography (CT) or X-ray imaging system using an initial image acquisition protocol to acquire an image of an anatomical region of interest of a patient using a corresponding predetermined number of scanning cycles during a predetermined scanning time period;
   a repository comprising:
   (i) an average contrast agent time to peak time period for a sample patient population based on time periods from when contrast agent concentrations substantially reach peak values in anatomical regions of interests of patients in the population relative to start times of contrast agent injections in the patients; and
   (ii) a plurality of predetermined different image acquisition protocols; each image acquisition protocol adapted to acquire the image of an anatomical region of interest of a patient using a corresponding predetermined number of scanning cycles during a corresponding predetermined scanning time period;
   a contrast agent peak time detector to detect a time that a contrast agent concentration substantially reaches a peak value in the anatomical region of interest of the patient; and
   an imaging processor to measure and record values associated with radiation attenuation and a presence of the contrast agent in the region of interest of the patient and to: (i) determine a contrast agent time to peak time period from a time of a start of contrast agent injection to the detected contrast agent peak time; (ii) compare, in response to a detection by the peak detector of a time for the contrast agent to peak in the patient region of interest, the contrast agent time to peak time period to the average contrast agent time to peak time period stored in the repository; (iii) determine whether the contrast agent time to peak time period exceeds or is lower than a predetermined difference threshold from the average contrast agent time to peak time period; (iv) adaptively select, in response to determining said detected contrast agent time to peak time period exceeds the predetermined difference threshold of the average contrast agent time to peak time period, a first image acquisition protocol from said plurality of predetermined image acquisition protocols, said first image acquisition protocol adapted to acquire the image of the anatomical region of interest of the patient using at least one of: (1) an extended scanning time period that is greater than the predetermined scanning time period of the initial image acquisition protocol; and (2) a number of scanning cycles that is greater than the predetermined number of scanning cycles of the initial image acquisition protocol; and (v) adaptively select, in response to determining said detected contrast agent time to peak time period is lower than the predetermined threshold of the average contrast agent time to peak time period, a second image acquisition protocol from said plurality of predetermined image acquisition protocols, said second image acquisition protocol adapted to acquire the image of the anatomical region of interest of the patient using at least one of: (1) a scanning time period that is less than the predetermined scanning time period of the initial image acquisition protocol; and (2) a number of scanning cycles that is less than the predetermined number of scanning cycles of the initial image acquisition protocol;
   where, in response to the adaptive selection of the first imaging protocol or the second imaging protocol, images of the anatomical region of interest of the patient are acquired by the imaging system of the at least one of the CT or X-ray imaging system using the first imaging protocol or the second imaging protocol, respectively.

2. A system according to claim 1, wherein said sample patient population comprises a population of patients based on demographic characteristics and medical conditions of the patient.

3. A system according to claim 2, wherein said demographic characteristics include at least one of: age, weight, gender and pregnancy status.

4. A system according to claim 2, wherein said medical conditions include at least one of: heart disease, impaired cardiac function and blood pressure.

5. A system according to claim 1, wherein in response to determining said detected contrast agent time to peak time period exceeds the predetermined difference threshold of the average contrast agent time to peak time period, said imaging processor selects a first image acquisition protocol adapted to cause at least one of the CT, X-ray and other imaging system to acquire the image using an increased time interval between scanning cycles that is greater than a time interval between the scanning cycles used in the initial image acquisition protocol.

6. A system according to claim 1, wherein in response to determining said detected contrast agent time to peak time period exceeds the predetermined threshold of the average contrast agent time to peak time period, said imaging processor selects a first image acquisition protocol adapted to cause at least one of the CT, X-ray and other imaging system to acquire the image using a reduced X-ray radiation tube voltage that is lower than an initial X-ray radiation tube voltage used in the initial image acquisition protocol.

7. A system according to claim 1, wherein the image processor is further configured to determine whether the contrast agent time to peak time period is equal to or lies within the predetermined difference threshold from the average contrast agent time to peak time period; and in response to determining said detected contrast agent time to peak time period is equal to or lies within the predetermined difference threshold from the average contrast agent time to peak time period, said imaging processor continues use of the initial image acquisition protocol without change.

8. A system according to claim 1, wherein in response to predetermined information indicating said patient has a hemi function impairment related condition, said imaging processor adaptively selects an image acquisition protocol from said plurality of predetermined image acquisition protocols adapted to cause at least one of the CT, X-ray and other imaging system to acquire the image of the anatomical region of interest of the patient using an extended scanning time period that is greater than the predetermined scanning time period of the initial image acquisition protocol.

9. A system according to claim 1, wherein said imaging processor adaptively selects one of said plurality of image acquisition protocols in response to data input parameters of a post processing method.

10. A system according to claim 1, wherein said imaging processor adaptively selects an image post-processing method in response to selecting one of said plurality of image acquisition protocols and known patient physiological status.

11. A computer implemented system for automatically adaptively selecting a medical image acquisition protocol usable by a Computed Tomography (CT) or X-ray imaging system, comprising:
  an imaging system of a Computed Tomography (CT), X-ray or other imaging system using an initial image acquisition protocol to acquire an image of an anatomical region of interest of a patient using a corresponding predetermined number of scanning cycles during a predetermined scanning time period;
  a repository comprising:
    (i) an average rate of contrast agent concentration change for a sample patient population; and (ii) a plurality of predetermined different image acquisition protocols, each image acquisition protocol adapted to acquire the image of an anatomical region of interest of patient using a corresponding predetermined number of scanning cycles during a corresponding predetermined scanning time period;
  a contrast agent change detector configured to detect a rate of contrast agent concentration change; and
  an imaging processor configured to measure and record values associated with radiation attenuation and a presence of the contrast agent in the region of interest of the patient and to: (i) compare, in response to a detection by the peak detector of a time for the contrast agent to peak in the patient region of interest, the detected rate of contrast agent concentration change to the average rate of contrast agent concentration change; (ii) determine whether the detected rate of contrast agent concentration change exceeds or is lower than a predetermined difference threshold; (iii) adaptively select, in response to determining said detected rate of contrast agent concentration change exceeds the predetermined difference threshold, a first image acquisition protocol from said image acquisition protocols in response to the comparison, the first image acquisition protocol adapted to acquire the image of the anatomical region of interest of the patient using at least one of: (1) a decreased scanning time period that is less than the predetermined imaging scanning time period of the initial image acquisition protocol; and (2) a number of scanning cycles that is lower than the predetermined number of scanning cycles of the initial image acquisition protocol; and (iv) adaptively select, in response to determining said detected rate of contrast agent concentration change is lower than the predetermined difference threshold from the average rate of contrast agent concentration change, said imaging processor selects a second image acquisition protocol from said plurality of predetermined image acquisition protocols, the second image acquisition protocol adapted to acquire the image of the anatomical region of interest of the patient using a scanning time period that is greater than the predetermined scanning time period of the initial image acquisition protocol;
  where, in response to the adaptive selection of the first imaging protocol or the second imaging protocol, images of the anatomical region of interest of the patient are further acquired by the imaging system of the at least one of the CT or X-ray imaging system using the adaptively selected first imaging protocol or the second imaging protocol, respectively.

12. A system according to claim 11, wherein said sample patient population comprises a population of patients based on demographic characteristics and medical conditions of the patient.

13. A computer implemented method for automatically adaptively selecting a medical image acquisition protocol usable by a Computed Tomography (CT) or X-ray imaging system, the method comprising:
  acquiring, by an imaging system of a Computed Tomography (CT) or X-ray imaging system using an initial image acquisition protocol, an image of an anatomical region of interest of a patient using a predetermined number of scan cycles during a predetermined scan time period;
  storing, in a repository: (i) an average contrast agent time to peak time period for a sample patient population based on time periods from when contrast agent concentrations substantially reach peak values in anatomical regions of interests of patients in the population relative to start times of contrast agent injections in the patients; and (ii) a plurality of predetermined different image acquisition protocols, each image acquisition protocol adapted to acquire the image of an anatomical region of interest of a patient using a corresponding predetermined number of scan cycles during a corresponding predetermined scan time period;
  detecting a contrast agent peak time a contrast agent concentration substantially reaches a peak value in the anatomical region of interest of the patient;
  determining a contrast agent time to peak time period from a time of a start of contrast agent injection to the detected contrast agent peak time;
  comparing, in response to the detection of a time for the contrast agent to peak in the patient region of interest, the contrast agent time to peak time period to the average contrast agent time to peak time period;
  determining the contrast agent time to peak time period is greater than a predetermined threshold of the average contrast agent time to peak time period;
  adaptively selecting a first image acquisition protocol from said plurality of predetermined image acquisition protocols, the first image acquisition protocol adapted to acquire the image of the anatomical region of interest of the patient using at least one of: (i) an extended scan time period that is greater than the predetermined scan time period of the initial image acquisition protocol; and (ii) a number of scan cycles that is greater than the predetermined number of scan cycles of the initial image acquisition protocol; and (iii) an increased time interval between the number of scan cycles that is greater than a time interval between the predetermined number of scan cycles used in the initial image acquisition protocol; and
  acquiring, in response to the adaptive selection of the first imaging protocol or the second imaging protocol, by the imaging system of the at least one of the CT or X-ray imaging system using the selected first image acquisition protocol.

14. A method according to claim 13, wherein said sample patient population comprises a population of patients based on demographic characteristics and medical conditions of the patient.

15. A method according to claim 13, further comprising:
in response to the determination that the contrast agent time to peak time period is greater than a predetermined threshold of the average contrast agent time to peak time period, adaptively selecting the first image acquisition protocol adapted to cause at least one of the CT, X-ray and other imaging system to acquire the image by further using a reduced X-ray radiation tube voltage that is lower than an initial X-ray radiation tube voltage used in the initial image acquisition protocol.

16. A method according to claim 13, further comprising:
determining the contrast agent time to peak time period is less than a predetermined threshold of the average contrast agent time to peak time period;
in response to the determination, adaptively selecting a second image acquisition protocol from said plurality of predetermined image acquisition protocols, the second image acquisition protocol adapted to acquire the image of the anatomical region of interest of the patient using at least one of: (i) a decreased scanning time period that is less than the predetermined scanning time period of the initial image acquisition protocol; and (ii) a number of scan cycles that is less than the predetermined number of scan cycles of the initial image acquisition protocol; and
acquiring, by the imaging system of the at least one of the CT, X-ray and other imaging system using the adaptively selected second image acquisition protocol, the image of the anatomical region of interest of the patient.

17. A method according to claim 13, further comprising:
selecting one of said plurality image acquisition protocols in response to data input parameters of a post processing method.

18. A system according to claim 13, further comprising:
adaptively selecting an image post-processing method in response to selecting one of said plurality of image acquisition protocols and known patient physiological status.

19. A computer implemented system for automatically adaptively selecting a medical image acquisition protocol usable by a Computed Tomography (CT) or X-ray imaging system, comprising:
an imaging system of a Computed Tomography (CT) or X-ray imaging system using an initial image acquisition protocol to acquire an image of an anatomical region of interest of a patient using a corresponding predetermined number of scanning cycles during a predetermined scanning time period;
a repository comprising:
(i) an average contrast agent time to peak time period for a sample patient population's based on time periods from when contrast agent concentrations substantially reach peak values in anatomical regions of interests of patients in the population relative to start times of contrast agent injections in the patients; and (ii) a plurality of predetermined different image acquisition protocols, each image acquisition protocol adapted to acquire the image of an anatomical region of interest of a patient using a corresponding predetermined number of scanning cycles during a corresponding predetermined scanning time period;
a contrast agent peak time detector to detect a time that a contrast agent concentration substantially reaches a peak value in the anatomical region of interest of the patient; and
an imaging processor to measure and record values associated with radiation attenuation and a presence of the contrast agent in the region of interest of the patient and to: (i) determine a contrast agent time to peak time period from a time of a start of contrast agent injection to the detected contrast agent peak time; (ii) compare, in response to a detection by the peak detector of a time for the contrast agent to peak in the patient region of interest, the contrast agent time to peak time period to the average contrast agent time to peak time period stored in the repository; (iii) determine whether the contrast agent time to peak time period exceeds a predetermined difference threshold from the average contrast agent time to peak time period; and (iv) adaptively select, in response to determining said detected contrast agent time to peak time period exceeds the predetermined difference threshold of the average contrast agent time to peak time period, a first Image acquisition protocol from said plurality of predetermined image acquisition protocol, wherein said first image acquisition protocol is adapted to acquire the image using a reduced X-ray radiation tube voltage that is lower than an initial X-ray radiation tube voltage used in the initial image acquisition protocol;
where, in response to the adaptive selection of the first imaging protocol or the second imaging protocol, images of the anatomical region of interest of the patient are further acquired by the imaging system of the at least one of the CT or X-ray imaging system using the first imaging protocol or the second imaging protocol, respectively.

20. A computer implemented method for automatically adaptively selecting a medical image acquisition protocol usable by a Computed Tomography (CT) or X-ray imaging system, the method comprising:
acquiring, by an imaging system of a Computed Tomography (CT) or X-ray imaging system using an initial image acquisition protocol, an image of an anatomical region of interest of a patient using a predetermined number of scan cycles during a predetermined scan time period;
storing, in a repository: (i) an average contrast agent time to peak time period for a sample patient population based on time periods from when contrast agent concentrations substantially reach peak values in anatomical regions of interests of patients in the population relative to start times of contrast agent injections in the patients; and (ii) a plurality of predetermined different image acquisition protocols, each image acquisition protocol adapted to acquire the image of an anatomical region of interest of a patient using a corresponding predetermined number of scan cycles during a corresponding predetermined scan time period;
detecting a contrast agent peak time a contrast agent concentration substantially reaches a peak value in the anatomical region of interest of the patient;
determining a contrast agent time to peak time period from a time of a start of contrast agent injection to the detected contrast agent peak time;
comparing, in response to the detection of a time for the contrast agent to peak in the patient region of interest, the contrast agent time to peak time period to the average contrast agent time to peak time period;

determining the contrast agent time to peak time period is greater than a predetermined threshold of the average contrast agent time to peak time period; and adaptively selecting a first image acquisition protocol from said plurality of predetermined image acquisition protocols, the first image acquisition protocol adapted to acquire the image of the anatomical region of interest of the patient using at least one of: (i) an extended scan time period that is greater than the predetermined scan time period of the initial image acquisition protocol; and (ii) a number of scan cycles that is greater than the predetermined number of scan cycles of the initial image acquisition protocol; and (iii) a reduced X-ray radiation tube voltage that is lower than an initial X-ray radiation tube voltage used in the initial image acquisition protocol; and acquiring, in response to the adaptive selection of the first imaging protocol or the second imaging protocol, by the imaging system of the at least one of the CT or X-ray imaging system using the selected first image acquisition protocol.

\* \* \* \* \*